United States Patent [19]
Hale et al.

[11] Patent Number: 5,144,831
[45] Date of Patent: Sep. 8, 1992

[54] METHOD AND APPARATUS FOR MONITORING GAS CONCENTRATIONS

[75] Inventors: John M. Hale, Meinier; Eugen Weber, Hinwil, both of Switzerland

[73] Assignee: Orbisphere Laboratories Neuchatel SA, Switzerland

[21] Appl. No.: 614,133

[22] Filed: Nov. 16, 1990

[30] Foreign Application Priority Data

Nov. 17, 1989 [CH] Switzerland ............ 4145/89

[51] Int. Cl.$^5$ ............................................. G01N 7/10
[52] U.S. Cl. .................. 73/19.05; 73/19.06; 73/19.1; 73/19.12
[58] Field of Search ............ 73/19.01, 19.05, 19.06, 73/19.1, 19.12, 31.07

[56] References Cited

U.S. PATENT DOCUMENTS

| | | | |
|---|---|---|---|
| 3,673,853 | 7/1972 | Griswold et al. | 73/19.1 |
| 3,731,523 | 5/1973 | Vissers et al. | 73/19.05 |
| 3,866,460 | 2/1975 | Pearce, Jr. | 73/19.05 |
| 3,871,228 | 3/1975 | Weiss | 73/19.05 |
| 4,365,505 | 12/1982 | Hölzl | 73/19 |
| 4,402,211 | 9/1983 | Sugawara et al. | 73/19.11 |
| 4,461,165 | 7/1984 | Kesson | 73/19.1 X |
| 4,516,580 | 5/1985 | Polanyi | 73/19.05 |
| 4,517,135 | 5/1985 | Szerenyi et al. | 73/19.1 X |
| 4,550,590 | 11/1985 | Kesson | 73/19.05 |

FOREIGN PATENT DOCUMENTS

0043229 11/1984 European Pat. Off.
0103988 11/1988 European Pat. Off.

Primary Examiner—Hezron E. Williams
Assistant Examiner—Michael Brock
Attorney, Agent, or Firm—Wigman & Cohen

[57] ABSTRACT

The concentration of a gas, such as carbon dioxide, in a fluid medium, such as an aqueous beverage, is monitored by pulsatingly measuring a specific parameter of diffusion of the gas through a membrane that is in contact with the fluid medium and is permeable for the gas but impermeable for the fluid; the gas is allowed to diffuse during a period of time into a receiving space of known volume; the amount of gas that diffuses into the receiving space is determined e.g. by measuring IR-absorption, heat conductivity, volume, pressure or the like physical parameters that depend upon the amount of gas in the volume; this yields a specific diffusion parameter or flux. The gas concentration of interest is then calculated from the specific parameter and a previously determined general parameter of diffusion of the gas through the membrane. Pulsating operation, i.e. a repeating sequence of cyclic removal and measuring phases, is characterized by relatively short phases; since, at the same time, the receiving space volume is relatively small while the gas permeability of the membrane is relatively low, reliable results can be obtained in quick response to concentration changes. The method can be applied for monitoring or for controlling the gas concentration by adding sufficient gas to maintain a desired gas concentration in the fluid medium.

10 Claims, 1 Drawing Sheet

METHOD AND APPARATUS FOR MONITORING GAS CONCENTRATIONS

BACKGROUND OF THE INVENTION

1. Field of the Invention

The invention generally relates to analytical methods and means; specifically, it relates to a method of monitoring the concentration of a gas in a fluid medium; further, the invention relates to an apparatus for carrying out the method combined or not with controlling the concentration of a gas in a fluid medium.

2. Prior Art

Numerous methods for monitoring gas concentrations are known and are frequently classified according to the measuring principles involved and/or the characteristic means used for separating the substance of interest from a mixture.

Accordingly, when using a membrane that is permeable for the substance of interest but impermeable to other components of the mixture, the term "membrane-based" analysis is appropriate. When membranes are used mainly because of their separating effect, e.g. between a gas, such as carbon dioxide, and a liquid, such as a carbonated beverage, maximum permeability of the membrane for the gas of interest is generally assumed to be desirable.

For example, a prior art membrane-based method of determining the concentration of carbon dioxide in a beverage, such as beer, as disclosed in EP 0 043 229 and EP 0 103 988, uses membranes that exhibit a maximum permeability for the gas of interest because the actual measuring parameter in these methods is the so-called equilibrium pressure that will build up within a membrane-enclosed chamber in response to the "concentration" (synonymous herein with "partial pressure") of the gas in a liquid that is "external" to the membrane-enclosed space. However, even with membranes made of silicone rubber which are notorious for their high permeability to gases, such as carbon dioxide, relatively long periods of time of typically in the order of 20 minutes may be required until equilibrium of gas pressures external and internal of the membrane-enclosed space is achieved. This method has been proposed for use in "controlling" the concentration of a gas, such as carbon dioxide, in a liquid, such as a beverage, i.e. maintaining a desired minimum concentration of the relatively costly carbon dioxide in a carbonated beverage by adding or "injecting" just those amounts of gas as are needed to maintain the required minimum concentration. Obviously, the results of such control will be determined to a large extent by the response and reliability of the measuring method used. And, while so-called "dynamic" pressure measuring methods are known, i.e. measuring a time-dependent pressure change and extrapolating the measured value or values towards infinity of time (and, hence, "perfect" equilibrium), such methods, though recommended for use in these prior art methods, tend to decrease reliability and reproducibility of the results for various reasons, e.g. because of mechanical deformations of the membrane under the impact of pressure and concurrent changes of chamber volume, membrane dimensions, permeability and other parameters that normally are expected to remain constant.

OBJECTS AND SUMMARY OF THE INVENTION

Accordingly, it is a main object of the invention to provide for a membranebased method of monitoring the concentration of a gas in a fluid medium providing for short response times and for reliable as well as reproducible results.

Another object of the invention is to provide for an improved and quickly responding method of controlling the concentration of a gas in a liquid medium.

Yet a further object of the invention is an apparatus suitable for use in performing the novel method of monitoring or controlling gas concentrations.

These and further objects apparent from the specification will be achieved according to the invention by a method of monitoring the concentration of a gas, such as typically carbon dioxide, in a fluid medium, such as typically a carbonated beverage, comprising the steps of:

(A) pulsatingly measuring a specific diffusion parameter of the gas through a polymer membrane that is in contact with the fluid medium and is permeable for the gas but is substantially impermeable for the fluid medium; and (B) calculating the concentration from a previously determined general diffusion parameter of the gas through the polymer membrane and said specific diffusion parameter.

According to another general embodiment the inventive method further includes the steps of:

(C) comparing the concentration obtained in the above mentioned step (B) with a predetermined concentration of the gas in the fluid medium; and (D) injecting an amount of the gas into the fluid medium so as to compensate a deficiency between the predetermined concentration and the concentration obtained in step (B).

According to another main embodiment the invention provides an apparatus for monitoring the concentration of a gas in a fluid medium by measuring a specific diffusion parameter of the gas through a polymer membrane that is in contact with the fluid medium and is permeable for the gas but is substantially impermeable for the fluid medium; the apparatus according to the invention comprises:

chamber means connected with the membrane for defining a predetermined receiving volume and for permitting diffusion of the gas through the membrane while preventing permeation of the fluid medium into the chamber means;

means operatively connected with said chamber means for determining the amount of gas that accumulates in the chamber means during a predetermined period of time (designated as measuring phase) by diffusion of the gas through the membrane into the chamber means;

means for removing, during a predetermined period of time (designated as a removal phase), substantially all of the gas that has diffused into the chamber means;

means for cyclically repeating the removal phase and the measuring phase while the method according to the invention is operated; and means for calculating the concentration of interest from a previously determined general diffusion parameter of the gas through the membrane.

PREFERRED EMBODIMENTS OF THE INVENTION

Generally, the entity termed "specific diffusion parameter" herein indicates a quantity of the gas of interest that diffuses or flows through the membrane per surface unit and per time unit.

Accordingly, the specific diffusion parameter is also termed "specific flux" and is then expressed in moles per square centimeter per second ($mol \cdot cm^{-2} \cdot s^{-1}$) By the same token, the term "general diffusion parameter" is the corresponding flux entity as determined previously by way of calibration, e.g. in the laboratory, for the particular or even individual membrane at a given pressure gradient; hence, "general flux" corresponds to the flux of the gas of interest at a given pressure gradient and can be expressed in terms of moles per square centimeter per second per bar ($mol \cdot cm^{-2} \cdot s \cdot bar^{-1}$).

In this context, the term "membrane" generally relates to layers, strata or films of organic polymers that are resistant to the conditions of operating the inventive method and permit diffusion of the gas of interest. Specific examples will be given below.

Operating conditions of the inventive method will generally be determined by the conditions of the fluid that contains the gas of interest, e.g. beer or other beverages containing carbon dioxide. Hence, temperatures between the freezing temperature of the fluid and the boiling point thereof, typically in the range of from about $-5°$ C. to about $\pm 100°$ C., and typical fluid pressures of, say, 2-20 bars or more are mentioned by way of illustration.

In a generally preferred embodiment of the invention a predetermined receiving volume for the gas is maintained in separation from the fluid medium by the membrane to permit diffusion of the gas of interest through the membrane; a means that is indicative of a quantity or mass of the gas in the receiving volume is operatively associated with said receiving volume to determine the diffused gas quantity of the flux parameter.

Basically, any prior art means that is capable of correlating an amount of gas with a measurable physical or chemical property of said gas could be used in the invention; for example, various forms of energy transport, emission or absorption properties, e.g. infrared absorption, thermal conductivity, absorptic of sonic or supersonic vibrations, chemical reactions, etc., by the gases of interest are well known in the art and can be used in the context of the present invention. Volumetric measurements, i.e. those measuring a volume of a gas at a given pressure, as well as barometric measurements, i.e. those measuring the pressure of a given volume of gas, can be used. Various prior art pressure measuring means that are commercially available provide for high precision results with relatively simple and reliable probes, e.g. transducers and, hence, represent typical yet in no way limiting examples.

Generally, the term "pulsating" as used herein for what is believed to be an essential requirement of the invention is intended to refer to a regular or cyclic sequence of alternating conditions for (1) removal of gas from a known receiving space or chamber, (2) subsequent diffusion of the gas through the membrane into the evacuated receiving space or chamber and measuring the amount of gas therein, and subsequent repetition of conditions (1) and (2) as long as the inventive method is operated. For brevity, the gas removing part of the pulsating operation according to the invention is termed "removal phase" and may imply a "degree of absence" of the gas corresponding to "vacuum" (absolute pressure near zero). However, achieving vacuum or near vacuum conditions in the receiving volume is not critical and mere venting, e.g. by periodic connection with the ambient, may be sufficient to achieve "removal", notably if venting is combined with flushing or purging of the receiving volume, e.g. with a suitably "inert" gas, such as nitrogen or ambient air.

While gas removal by periodic evacuation of the receiving volume, e.g. by on-and-off connection of the chamber to a vacuum pump or by venting, is a preferred method of removing the diffused gas from the chamber because of simplicity of these methods, this is more a matter of convenience rather than principle. Other gas removal methods including chemical reaction, absorption, etc. could be used depending upon the reactivity of the gas of interest or the reaction kinetics involved. With the preferred small volumes of the receiving space and low-permeation membranes exemplified below a substantially complete removal of the gas during the removal phase can be achieved with ordinary laboratory pumps within a few seconds. While the diffusion phase will generally require a longer time period than the removal phase, it will frequently be in the order of one or a few, say, 1 to 4 minutes. A sufficient degree of precision of time control for the predetermined length of the alternating phase is well within the competence of one skilled in the art and requires no further explanation herein.

Those intermediate phases of pulsating operation in which the gas is allowed to diffuse into the receiving volume and in which the amount of gas in that volume is determined are termed "measuring phases". Any measuring phase may include one or more individual determinations of the gas quantity, preferably with intermittent periods of evaluation. In practice, a measuring phase might include alternating periods of measurement and evaluation and each measuring period may include a plurality of, say, 10 to 20 measurements.

For example, a measuring phase of 60 seconds duration might include ten measuring periods of 3 seconds duration each with alternating evaluation periods, also of 3 seconds duration each; 15 measurements might be made during each measuring period so that 150 measurements could be made during one measurement phase.

The net flux is the difference between partial fluxes of gas through the membrane in opposite directions. It is a maximum immediately after termination of the removal phase and decreases with time throughout the measurement phase, due to an increase in the partial flux from the receiving volume into the fluid medium. It is preferable that each measurement phase be terminated while the net flux is relatively high, say, amounting to more than 10 % of its maximum value under the specific conditions, preferably more than 90 % of its maximum value and up to 100 % thereof. Optimization may require a few simple tests. Generally, the membrane is selected to provide for a flux in the range of from $1 \cdot 10^{-8}$ to $1 \cdot 10^{-10} mol \cdot cm^{-2} \cdot s^{-1}$. When the gas quantity is determined in terms of pressure, membranes that provide for a rate of increase in the range of from 0.1 to 10 millibars per second are preferred. Accordingly, highly permeable membranes such as those made of silicone rubber are not preferred for use in the invention.

For a preferred application of the method according to the invention, i.e. measurement of the concentration (partial pressure) of carbon dioxide in a gaseous or liquid external phase, e.g. in connection with the production of beer or sparkling wine and the processing of non-alcoholic carbonated beverages, the typical membrane materials are by way of example halocarbon polymers, such as polyfluoroalkoxy polymer (PFA), fluoroethylene (PTFE) and ethylenefluoroethylene (ETFE) copolymer. Typical membrane thicknesses lie in the range of 5 to 100 micrometers, wherein thicknesses of 10 to 30 micrometers are preferred. The surface area of the membrane may be matched to the conditions within wide limits and lies typically in the range of 5 to 2000 mm$^2$. Such membranes resist a wide range of aggressive chemicals and are, furthermore, tolerant of extreme temperature (e.g. $-50°$ to $+250°$ C.) and pressure conditions.

Further, it follows from the equations shown herein that receiving volumes as low as possible are to be preferred, for example, less than 1 ml and preferably less than 0.25 ml. In consequence, the metallic, preferably stainless steel, glass or ceramic, sintered or woven body which is used to support the membrane must also have the lowest possible volume. A typical and suitable support is a stainless steel gauze woven from very fine wires, typically 30 microns thick, in the form of a thin disc.

Gases other than $CO_2$ whose concentrations or partial pressures in a fluid medium may be determined according to the method of the invention are simple permanent gases, such as molecular hydrogen, helium, oxyen and nitrogen, as well as other gases, such as hydrogen sulfide, chlorine and sulfur dioxide, which are characterized by elevated solubility in typical membrane materials.

The flux as well as the temperature needed for the purpose of temperature compensation noted herein is preferably determined continuously by means of a correspondingly programmed computer. This device can also determine the durations of removal and measurement phases, and perform all calculations required for translation of flux, e.g. in terms of the rate of pressure rise ($dP/dt$), into an estimate of the concentration of the gas of interest in the fluid medium. Finally, the computer can arrange automatic determination of the general diffusion parameter for gas flux into the receiving volume during a calibration operation. Such reference values may be permanently recorded in the computer memory so that the output value is indicated or read-off or recorded directly in corresponding concentration units. Suitable devices of this type are known per se and require no further description.

BRIEF DESCRIPTION OF THE DRAWINGS

The invention will be explained, without limitation in more detail by reference to the enclosed drawings illustrating some preferred embodiments and in which.

DETAILED DESCRIPTION OF THE DRAWINGS

Figure 1:
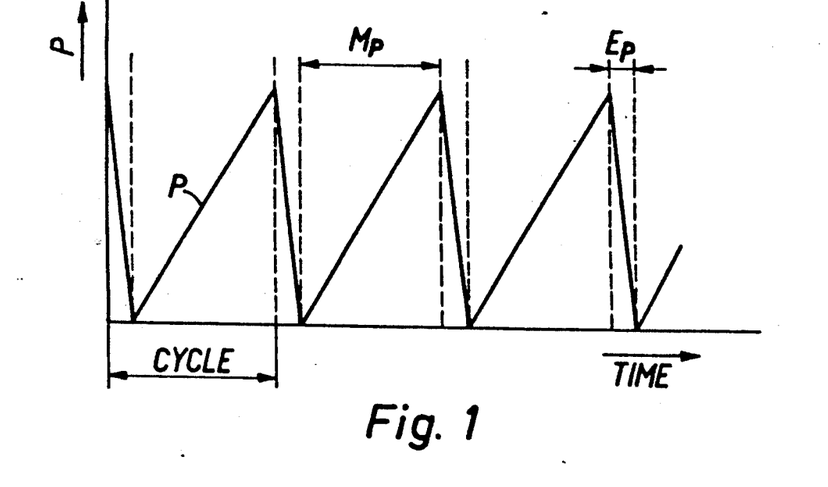
FIG. 1 is a schematic representation of the variation of the internal gas pressure in a constant receiving volume during the relatively rapidly alternating removal and measurement phases in the pulsating measurement process according to the invention.

In the diagram shown in FIG. 1 the absolute gas pressure in the interior of the receiving volume is applied to the ordinate (in arbitrary units) and the time is applied to the abscissa (also in arbitrary units). Examples are given below of typical pressure and time values in the performance of the method according to the invention: the removal phases EP have a constant duration of about 1 to 50 seconds and should in each case be sufficiently long to remove substantially all the gas present in the receiving volume by connection to a source of vacuum, preferably a permanently operating oil or air driven vacuum pump, for example as is used on a laboratory scale in vacuum distillation processes. At the end of the automatically timed removal phases, the connection to the vacuum is interrupted, for example by means of a magnetically actuated valve, and the measurement phases MP, also of constant duration, begin.

Figure 2:
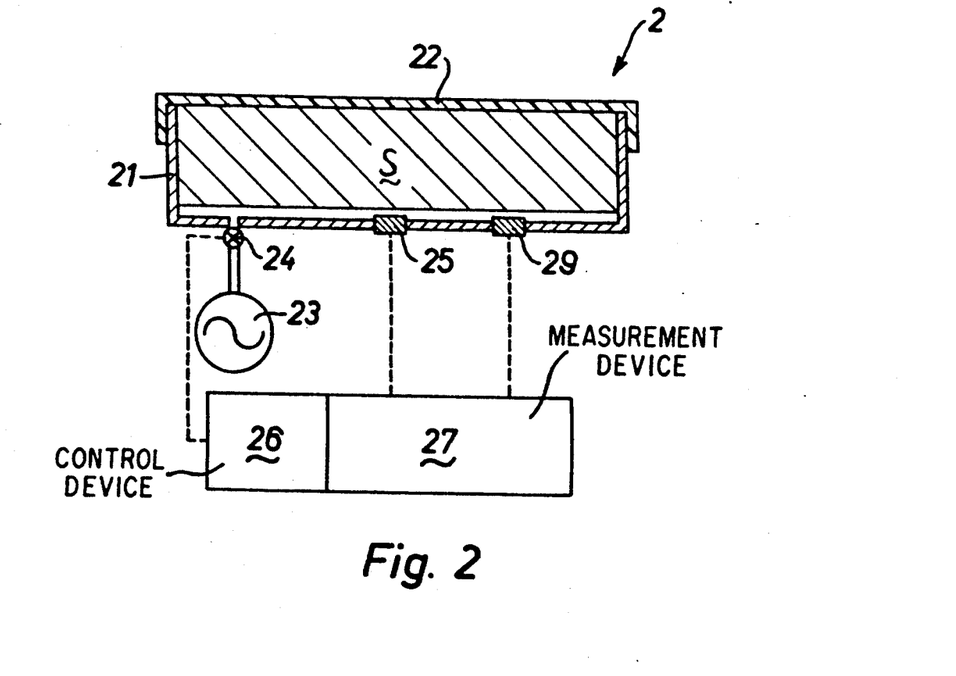
FIG. 2 is a schematic view of a preferred apparatus according to the invention.

FIG. 2 illustrates schematically an apparatus 2 for carrying out the method according to the invention with a receiving volume 21 which is isolated from the fluid medium by a membrane 22 of the below mentioned type. The membrane is sealed to an opening in the receiving volume, such that those constituents of the fluid medium unable to permeate through the membrane are effectively excluded from the receiving volume. The internal volume of chamber 21 is held constant for all pressure fluctuations that may be expected in practice by means of a corresponding supports of the membrane, e.g. with a gauze or frit as explained above. The chamber 21 is connected with a source 23 for reduced pressure, e.g. with a conventional vacuum pump wherein the connection, e.g. at the opening into the receiving volume, there is a device 24, e.g. an electromagnetically controlled valve, for interrupting the connection between the source 23 of the reduced pressure and the chamber 21. A pressure sensor 25 is provided in the interior of the chamber 21 or is connected therewith. A conventional time switch may serve for the periodic actuation of the control device 26, but it is preferred to use a computer as explained below. The measurement device 27 serves to capture the behavior in time of the pressure change in the chamber 21, preferably also with the values generated by the temperature sensor 29 for temperature compensation. In general, the control and analyzing device is preferably an integral appliance.

Generally, the receiving volume 21 is sealed against liquid entry with membrane 22, the outer side of which is in contact with the fluid (i.e. gaseous or liquid) medium which contains a gas of which the partial pressure is to be determined. The gas contained, that is, mixed or dissolved, in the medium diffuses or permeates through the membrane, accumulating in the receiving volume and causing the pressure to rise at a rate which is most conveniently in the range of 0.1 to 10 mbar per second.

If this process were to continue indefinitely, a state of equilibrium would eventually be reached in which the partial pressures of all components of the fluid medium able to permeate through the membrane would be identical inside the receiving volume and in the fluid medium. In this state, no net transfer of gas would take place, that is to say, the rate of transfer of gas from the fluid into the receiving volume would be identical to the rate of transfer in the opposite direction. Also in this state, the total gas pressure in the receiving volume would be constant and no pressure rise would be observed. In the simplest case of a single permeating component, a measurement of the total gas pressure inside the receiving volume would then enable determination of the concentration of that gas in the fluid medium. A number of devices for the measurement of gas concentrations in gaseous and liquid media have been described in the prior art based on this principle.

According to the method of this invention, however, long before such an equilibrium is attained, e.g. after 2 to 300 seconds, typically after 60 seconds, the measurement phase is automatically terminated in that the connection with the vacuum source is restored and the gas which has accumulated in the receiving volume is drawn off. The duration of the measurement phase is therefore characterized by the fact that equilibrium is never reached during normal operation. It is also preferable that the measurement phases be at least about three times and even more preferably at least about ten times longer than the normally very short removal phases.

The measurement magnitude or parameter of the gas of interest, whose partial pressure in the medium is to be determined, is here, in contrast to the state of the art, not the equilibrium pressure that is attained in the receiving volume, but rather the rate of pressure change, i.e. the "steepness" of the rising flank of the measurement pulse MP in FIG. 1. In more precise mathematical terms, it is the derivative with respect to time of the internal pressure measurement and indicates a specific flux of gas into the volume.

The gas amount present in the interior of the receiving volume may be measured with a pressure sensor of a type known per se which is arranged directly in the receiving volume or is in as direct a connection therewith as is possible (i.e. of which the connection has the lowest possible volume). The change takes place according to the following equation which is used in practice to calculate the partial pressure of the gas of interest in the fluid medium:

$$\text{flux} = \frac{dn}{dt} = \frac{V \cdot dP_i}{R \cdot T \cdot dt} = \frac{D \cdot S \cdot a}{b}(P_a - P_i)$$

or: $(dP_i/dt) = (P_a - P_i)/\gamma$ wherein $P_a$ is the external pressure or partial pressure to be determined and $P_i$ is the pressure of the gas prevailing in the receiving volume, $(dP_i/dt)$ is the time derivative of the internal pressure. $\gamma$ is a time constant which is a general diffusion parameter in the sense described above which in turn is determined according to the invention by the equation:

$\gamma = b \cdot V/(R \cdot T \cdot S \cdot A \cdot D)$ wherein:
b = the thickness of the membrane
A = the surface area of the membrane
V = the volume of the receiving volume
S = the solubility of the gas in the material of the membrane
D = the coefficient of diffusion of the gas in the material of the membrane
T = the temperature and
R = the universal gas constant.

As mentioned above, it is most convenient from the practical point of view if the gas to be determined diffuses through the membrane under the given method conditions a rate of $1 \cdot 10^{-8}$ to $1 \cdot 10^{-10}$ (mol·cm$^{-2}$·s$^{-1}$) or, in terms of pressure increase $(dP_i/dt)$, of from 0.1 to 10 mbar per second. From the above equations it follows that this rate depends upon the concentration or partial pressure of gas in the fluid medium $P_a$ and upon the time constant $\gamma$. The latter, in turn, depends upon the material, area and thickness of the membrane as well as upon the temperature. The rate of pressure rise may be determined by a few simple experiments and is related as follows to membrane permeabilities quoted by the membrane manufactures.

TABLE 1

| | Approximate Membrane Permeabilities | | | |
|---|---|---|---|---|
| | MEMBRANE | | | |
| Gas | Silicone | PFA | PTFE | ETFE |
| $CO_2$ | 1800 | 14 | 4.9 | 5.0 |
| $O_2$ | 382 | 6.2 | 2.4 | 1.2 |
| $N_2$ | 90 | 2.4 | 1.4 | 0.4 |

Units of measurement: $10^{-8} \cdot $ cm$^3$(STP) $\cdot$ cm/(sec $\cdot$ bar $\cdot$ cm$^2$)
PFA = perfluoroalkoxy polymer
PTFE = polytetrafluoroethylene
ETFE = ethylenetetrafluoroethylene copolymer The Table lists permeabilities of some common membranes for carbon dioxide, oxygen and nitrogen. The quantity of gas quoted diffuses through a membrane of 1 cm thickness, 1 cm$^2$ area, in one second, when the difference of partial pressures of the gas applied to the opposite faces of the membrane is maintained at 1 bar.

If these figures are divided by the molar volume, 22400 cm$^3$ per mole, one derives the number of moles of gas diffusing through such a membrane per second (dn/dt).

Suppose this gas accumulates in a receiving volume V cm$^3$. The rate of pressure rise in the volume, from the ideal gas law, is then $(dp/dt) = (RT/V)(dn/dt)$.

EXAMPLE 1

Taking the case of $CO_2$ diffusing through PFA at 0° C. it is found from the above Table that:

$(dn/dt) = 6.25 \cdot 10^{-12}$ moles per second

Hence, if this gas accumulates in a 1 cm$^3$ receiving volume under the process conditions of 1 bar pressure difference, 0° C., 1 cm thick membrane, 1 cm$^2$ membrane area, the rate of pressure rise is $(dp/dt) = 6.25 \cdot 10^{-12} \cdot 83 \cdot 273/1 = 1.4 \cdot 10^{-7}$ bars per second This would be only the initial rate of pressure rise at constant external pressure because the pressure difference across the membrane would fall with the rise in internal pressure. It is for this reason that a differential equation is used in practice to describe the actual pressure change inside the receiver.

Such a low rate of pressure rise would be very difficult to measure with precision, and therefore lies outside the recommended band of values specified in this invention. It is possible to speed up the rate of pressure rise by choosing appropriately the thickness and area of the membrane, for example, by using a membrane of thickness $25 \cdot 10^{-4}$ cm and area about 3 cm$^2$. Then, the rate of pressure rise becomes:

$(dp/dt) = 1.4 \cdot 10^{-7} \cdot 3/(25 \cdot 10^{-4}) = 0.17$ mbar/sec which is easily measurable, and within the recommended band.

In practice, the temperature of the fluid medium may not be controllable, and there is a need to compensate the measured rate of pressure rise for variations of temperature. Such a need is imposed by the strong temperature dependence of the solubility S and diffusion coefficient D of the gas of interest in the membrane material.

EXAMPLE 2

This example illustrates flux measurement in terms of the rate of change of the quantity of gas accumulated in the measuring chamber by measurement of the volume of gas at constant pressure.

A measuring chamber of the previously described type is provided with a gas-tight microliter syringe of which the plunger position is controlled by a stepping motor. During the measurement phase, pulses are sent to the stepping motor causing the piston to be withdrawn such that the measurement volume increases. The frequency of these pulses is adjusted such that the pressure of the gas in the measurement chamber remains constant.

At the end of the measurement phase, the solenoid valve is opened, but instead of evacuating the gases in the measuring chamber, the piston of the syringe is moved inwards such that the gases are expelled through the valve. Then the solenoid valve is closed once more and the cycle recommences.

What is measured is the rate of change of volume, dV/dt, necessary to maintain the gas pressure constant in the measurement chamber. From this, the rate of change of the quantity of gas in the measurement chamber can be calculated:

$$\frac{dn}{dt} = \frac{p}{RT} \cdot \frac{dV}{dt} = \frac{DSA}{b}(P-p)$$

wherein:
n is the number of moles of gas in the measurement chamber
t is the time
p is the (constant = atmospheric) pressure of gas inside the measurement chamber
P is the pressure of gas acting on the outer face of the membrane which needs to be determined
D is the diffusion coefficient, and
S is the solubility of the gas in the membrane material
A is the area and
b is the thickness of the membrane
R is the gas constant
T is the absolute Kelvin temperature.

EXAMPLE 3

This example illustrates the use of a balance ("Quartz Micro Balance") to determine the quantity of gas in the measurement chamber.

A piezoelectric AT-cut quartz crystal vibrates in shear mode when excited electrically at a frequency which depends upon the mass of the crystal. A coating is applied on its surface which selectively absorbs or adsorbs the gas such that the mass of the whole crystal is augmented by the mass of the immobilized gas. The sensitivity of the device is such that nanograms of gas can be detected.

A crystal so prepared is exposed to the gas which accumulates in the measurement chamber during the measurement phase. A continuous variation is observed in the vibration frequency of the crystal. The extent of the shift is a measure of the quantity of gas immobilized on the crystal surface which under conditions of the Langmuir isotherm is furthermore a measure of the quantity of gas enclosed in the measurement chamber. Langmuir conditions are enforced by keeping the total gas pressure low inside the measurement chamber. Additionally, periodic evacuation, together with a heating of the quartz crystal, causes desorption of the gas from the crystal and, hence, reestablishment of the initial conditions.

EXAMPLE 4

This example illustrates electrochemical detection of the carbon dioxide. The quantity of carbon dioxide accumulating in the measurement chamber by diffusion out of a carbonated beverage can be determined by means of an electrochemical detector such as described by Severinghaus, J. W., and Bradley, A. F., J. Appl. Physiol. 13, 515–520 (1958) in which the $CO_2$ diffuses through a membrane and equilibrates with a small volume of water of which the pH is monitored by means of a glass electrode. The concentration of $CO_2$ in the measurement volume can be determined in this manner.

EXAMPLE 5

This example illustrates a thermal conductivity method of detection of carbon dioxide.

A miniature solid-state, monolithic thermal conductivity detector(Hartman & Braun AG, Germany) was mounted in a receiving volume of 0.5 ml which was isolated from a flowing carbonated liquid by a teflon membrane, 0.0025 cm thick, 5 $cm^2$ area Inlet and outlet ports were provided which could be opened or closed by means of valves.

The operation consisted of an endless repetition of removal and measuring phases. During the 5 second long removal phases the ports were opened to permit purging of the receiving volume with air at a flow rate of about 1 ml per second. At the end of each removal phase the ports were closed in the sequence inlet followed by exit so that air at atmospheric pressure was enclosed in the receiving chamber. The thermal conductivity signal was followed and recorded during the ensuing 60 second long measuring phases. It was noticed that the form of the response of the thermal conductivity detector changed imperceptibly when the outlet port was left open to the atmosphere during the measuring phase because, in practice, there was very little flux of gas through the membrane, the signal from the thermal conductivity detector was independent of total gas pressure under the conditions of use and very little mixing of gas with air occurred through the outlet port.

Carbon dioxide and water vapor diffused from the liquid through the membrane into the receiving volume and, simultaneously, oxygen and nitrogen diffused out of the receiving volume through the membrane into the liquid during the measuring phases. The diffusion rate of $CO_2$ was about 5 microliters per minute per bar partial pressure difference of $CO_2$ across the membrane at 25° C. The signal from the thermal conductivity detector initially corresponded to that of pure air but fell with the passage of time due to the replacement of highly conducting $O_2$ and $N_2$ by less well conducting $CO_2$. From the magnitude of this signal it was possible to compute the fraction of $CO_2$ in the gas mixture in the receiving volume at all times. In turn, the partial pressure of $CO_2$ in the liquid was computed with the aid of a model from the rate of gas transport in the system. It was found that partial pressures in the range of from 10 mbar to several bars could be measured in this fashion with excellent reproducibility and precision. Measurements were unaffected by hydrostatic pressure in the liquid and temperature effects were easily compensated.

Any apparatus generally described above can be combined with a device (e.g. a valve) to regulate the injection of the gas of interest into the fluid medium, and an electronic controller of the type known per se (e.g. a PID controller) in order to control the concentration of gas dissolved in a liquid or the fraction of a given gas contained in a gas mixture. Equipment for carrying out such a control function is readily available and its operating principles are well known to persons skilled in the art and need not be described in detail. The method is based on a comparison of the gas partial pressure in the fluid medium measured at a point downstream from the injection point with a set point or reference value, that is to say, the desired gas partial pressure in the fluid. The latter quantity may need to be calculated from a desired dissolved gas concentration in a liquid medium by appeal to the known thermodynamic characteristics of the gas-liquid equilibrium. In the case of carbonated aqueous beverages, for example, Henry's Law describing the solubility of the gas in the water at the temperature of the beverage provides the necessary relation. The control apparatus generates an output proportional to the difference between the above compared quantities which then controls the degree of opening of the above mentioned valve.

In general, the invention offers significant advantages over the equilibrium type of measurement apparatus mentioned above. In particular, there is a shortening of the response time from typically 10 minutes to typically 10 seconds. This advantage is extremely valuable in control applications where speed of response to concentration changes is of prime importance. A second advantage when operating with vacuum removal stems from the fact that the interior of the receiving volume is always at a reduced pressure compared to the pressure in the fluid medium. This eliminates a problem of prior art apparatus, i.e. that of membrane inflation which occurs when the receiving volume has equilibrated with a high gas pressure and the gas partial pressure in the fluid suddenly falls. Another advantage, again with vacuum removal, is apparent when the concentration of dissolved gas in an aqueous solution is to be determined: This is the safe prevention of water condensation inside the receiving volume due to the frequent evacuation of gas including water vapor.

Various modifications of the described embodiments will be apparent within the scope of the invention for a man skilled in the art.

Accordingly, what we claim is:

1. A method of monitoring the concentration of a gas in a fluid medium comprising the steps of:
    (A) pulsatingly measuring a specific diffusion parameter per unit area and per unit time of said gas through a polymer membrane that is in contact with said fluid medium and is permeable for said gas but substantially impermeable for said fluid medium, said measuring occurring prior to diffusion of said gas reaching equilibrium; and
    (B) calculating said concentration from a previously determined general diffusion parameter of said gas through said polymer membrane and said specific diffusion parameter.

2. A method of monitoring the concentration of a gas in a fluid medium comprising the steps of:
    (A) pulsatingly measuring a specific diffusion parameter per unit area and per unit time of said gas through a polymer membrane that is in contact with said fluid medium and is permeable for said gas but substantially impermeable for said fluid medium; and
    (B) calculating said concentration from a previously determined general diffusion parameter of said gas through said polymer membrane and said specific diffusion parameter;
    (C) maintaining a predetermined receiving volume for said gas in separation from said fluid medium by said polymer membrane to permit diffusion of said gas through said membrane; operatively associating with said receiving volume a means that is indicative of a quantity of said gas within said receiving volume;
    (D) said pulsatingly measuring of said specific diffusion parameter in step (a) comprising the steps of:
        (A-1) removing, during a predetermined period of time designated as a removal phase, substantially all of said gas that has diffused into said receiving volume;
        (A-2) subsequently allowing, during a predetermined period of time designated as a measuring phase, said gas to accumulate in said receiving volume by diffusion through said polymer membrane, said predetermined period of time being less than the time required for said diffusion to reach equilibrium;
        (A-3) determining the amount of gas that accumulates, during the amount of gas that receiving volume by diffusion through said polymer membrane; and
        (A-4) cyclically repeating said steps (A-1), (A-2), and (A-3) during said monitoring of said concentration.

3. The method of claim 2 wherein said removing is effected by a vacuum source connected to said receiving volume during each removal phase.

4. The method of claim 2 wherein said means that is indicative of said quantity of said gas in said receiving volume is a volumetric device.

5. The method of claim 3 wherein said means that is indicative of said quantity of said gas in said receiving volume is a device for measuring an energy adsorption or transportation parameter of said gas.

6. The method of claim 3 wherein said means that is indicative of said quantity of said gas in said receiving volume is a barometric device.

7. The method of claim 3 wherein said measuring phase is limited so as to provide for a gas flux in the range of from 10–100% of its maximum volume.

8. The method of claim 2 wherein said membrane is selected to provide for a maximum flux of gas in the range of from $1 \cdot 10^{-8}$ to $1 \cdot 10^{-10}$ (mol·cm$^{-2}$·s$^{-1}$).

9. An apparatus for monitoring the concentration of a gas in a fluid medium by measuring a specific diffusion parameter per unit area and per unit time of said gas through a polymer membrane that is in contact with said fluid medium and is permeable for said gas but is substantially impermeable for said fluid medium; said apparatus comprising:
    chamber means connected with said membrane for defining a predetermined receiving volume and for permitting diffusion of said gas through said membrane while preventing permeating of said fluid medium into said chamber means;

means in operative connection with said chamber means for determining the amount of gas accumulated, during a predetermined period of time designated as a measuring phase, said predetermined period of time being less than the time for said diffusion to reach equilibrium, by diffusion of said gas through said membrane into said chamber means;

means for removing, during a predetermined period of time designated as a removal phase, substantially all of said gas that has diffused into said chamber means;

means for cyclically repeating said removal phase and said measuring phase; and means for calculating said concentration from a previously determined general diffusion parameter of said gas through said polymer membrane.

10. The method of claim 7, wherein said gas flux is in the range of from 90 to 100% of its maximum value.

* * * * *

UNITED STATES PATENT AND TRADEMARK OFFICE
CERTIFICATE OF CORRECTION

PATENT NO. : 5,144,831
DATED : September 8, 1992
INVENTOR(S) : John M. Hale et al It is certified that error appears in the above-indentified patent and that said Letters Patent is hereby corrected as shown below:

Column 2, line 5, "membranebased" should be --membrane based--.

Column 3, line 10 before "By" insert --.--;
line 30, "$^+$ 100° C" should be --± 100° C--;
line 46, "absorptic" should be --absorption--.

Column 5, line 59, after "limitation" insert --,--.

UNITED STATES PATENT AND TRADEMARK OFFICE
CERTIFICATE OF CORRECTION

PATENT NO. : 5,144,831
DATED : September 8, 1992
INVENTOR(S) : John M. Hale et al It is certified that error appears in the above-indentified patent and that said Letters Patent is hereby corrected as shown below:

Column 6, line 31, "supports" should be --support--.

Column 8, line 8, "manufactures" should be --manufacturers--.

Column 10, line 31, after "area" insert --period--.

Column 12, claim 2, line 35, "the amount of gas that" should be --said measuring phase, in said--.

Signed and Sealed this

Seventh Day of December, 1993

Attest:

BRUCE LEHMAN

Attesting Officer    Commissioner of Patents and Trademarks